(12) United States Patent
Kwon et al.

(10) Patent No.: US 8,551,727 B2
(45) Date of Patent: Oct. 8, 2013

(54) GOLD NANOPARTICLE BASED PROTEASE IMAGING PROBES AND USE THEREOF

(75) Inventors: Ick-Chan Kwon, Seoul (KR); Kui-Won Choi, Seoul (KR); Kwang-Meyung Kim, Seoul (KR); Cheol-Hee Ahn, Seoul (KR); In-Chan Youn, Seoul (KR); Seul-Ki Lee, Seoul (KR); Kyeong-Soon Park, Jeollanam-Do (KR)

(73) Assignee: Korea Institute of Science and Technology (KR)

( * ) Notice: Subject to any disclaimer, the term of this patent is extended or adjusted under 35 U.S.C. 154(b) by 805 days.

(21) Appl. No.: 12/595,078

(22) PCT Filed: Apr. 10, 2008

(86) PCT No.: PCT/KR2008/002021
§ 371 (c)(1),
(2), (4) Date: Oct. 8, 2009

(87) PCT Pub. No.: WO2008/127019
PCT Pub. Date: Oct. 23, 2008

(65) Prior Publication Data
US 2010/0124757 A1    May 20, 2010

(30) Foreign Application Priority Data
Apr. 11, 2007    (KR) .................. 10-2007-0035722

(51) Int. Cl.
| | | |
|---|---|---|
| *C12Q 1/37* | (2006.01) | |
| *C12Q 1/34* | (2006.01) | |
| *B82B 3/00* | (2006.01) | |
| *C12N 11/14* | (2006.01) | |
| *C12N 11/18* | (2006.01) | |

(52) U.S. Cl.
USPC ............. 435/23; 435/24; 435/174; 435/176; 977/773; 977/774

(58) Field of Classification Search
USPC .................. 435/23, 24, 174, 176; 977/773, 977/774
See application file for complete search history.

(56) References Cited

U.S. PATENT DOCUMENTS

2011/0014125 A1* 1/2011 Bossmann et al. ............. 424/9.1

FOREIGN PATENT DOCUMENTS

KR    10-0704548    4/2007

OTHER PUBLICATIONS

Hsieh et al. 2007. Localized Surface Plasmon Coupled Fluorescence Fiber-Optic Biosensor with Gold Nanoparticles. Analytical Chemistry, vol. 70, No. 9, pp. 3487-3493.*
Medintz et al. 2006. Proteolytic activity monitored by fluorescence resonance energy transfer through quantum-dot-peptide conjugates. Nature Materials, vol. 5, pp. 581-589.*
Emonard et al. 1990. Matrix Metalloproteinases. A Review. Cellular and Molecular Biology, vol. 36, No. 2, pp. 131-153.*
2004 IUBMB Collagenase=MMP.*
Chang, E., et al., *Biochemical and Biophysical Research Communications*, v. 334, No. 4, 2005, pp. 1317-1321.
Lee, Seulki et al., "A Near-Infrared-Fluorescence-Quenched Gold-Nanoparticle Imaging probe for In Vivo Drug Screening and Protease Activity Determination", Angewandte Chemie Int Ed (2008) 47, 2804-2807.
Zhao, W. et al., "*Enzymatic Cleavage of Nucleic Acids on Gold Nanoparitles: A Generic Platform for Facile Colorimetric Biosensors*", Small, vol. 4, No. 6, 2008, pp. 810-816.

* cited by examiner

*Primary Examiner* — Jon P Weber
*Assistant Examiner* — Kailash C Srivastava
(74) *Attorney, Agent, or Firm* — Ostrolenk Faber LLP (57) ABSTRACT

Disclosed are a metal nanoparticle onto which a peptide substrate specifically degraded by protease and fluorophore are chemically modified for selectively imaging protease expressed in cell and in tissue in a human body, and the use thereof. Also, a quantitative analysis method of protease using the metal nanoparticle, a cell imaging method and a drug screening method of inhibiting a protease overexpression are provided. In detail, the present invention is directed to a metal nanoparticle having a peptide substrate and fluorophore coupled thereto, the peptide substrate and the fluorophore being specifically degraded by due to a protease activated in various ways in cell and in a human body to exhibit fluorescence. Hence, the metal nanoparticle can be used to rapidly screen activation and inhibition of the protease in the imaging manner. Also, the metal nanoparticle is capable of being selectively absorbed into a cell and a tissue so as to be possibly used as a sensor for real-time cell imaging and early diagnosis of non-invasive diseases.

9 Claims, 5 Drawing Sheets

0    1.4    3.5    7    14
MMP-2 Conc. (nmol/L)

+ Inh.    - Inh.

GOLD NANOPARTICLE BASED PROTEASE IMAGING PROBES AND USE THEREOF

CROSS-REFERENCE TO RELATED APPLICATIONS

The present application is a 35 U.S.C. §§371 national phase conversion of PCT/KR2008/002021, filed Apr. 10, 2008, which claims priority of Korean Patent Application No. 10-2007-0035722, filed Apr. 11, 2007. The PCT International Application was published in the English language.

TECHNICAL FIELD

The present invention relates to a metal nanoparticle having a peptide substrate specifically degraded by a protease and fluorophore coupled to the peptide substrate, capable of selectively imaging protease expressed in cell and in tissue in a human body, and the use thereof.

Also, the present invention relates to a quantitative analysis method of protease using the metal nanoparticle, a cell imaging method, and a drug screening method of inhibiting protease overexpression.

BACKGROUND ART

Proteolytic Enzymes (proteases) inhibit proteins activation or their fate based on hydrolysis of irreversible peptide bonds. Examples of such inhibition include the designation of positions of proteins inside or outside a cell, separation of proteins from a cellular surface, activation or deactivation of various types of growth factor hormone, cytokine and protease, conversion of agonist of receptor into antagonist, and the like. Thus, the protease serves to control various cell functions in a broad sense, which is achieved by digestion of bio-active materials. Therefore, the functional relation of the protease with life phenomena of all life is remarkably important. For example, deficiency or overexpression of a spatiotemporal protease causes fatal results, such as cancers, arthritides, neurodegenerative diseases, cardiovascular diseases and the like. Accordingly, the pharmaceutical industry concerns such proteases and their matrix proteins as major targets for new drug development to thusly give great interest therein.

Such various functions (roles) of the protease and recently completed different genome projects are introducing active investigations (searches) in the functions of the protease in a cell and in a human body. According to the human genome project, approximately more than 500 genes related to the protease were recognized among human genes. Recently, it is newly known that the protease plays a pivotal role in various types of human diseases, e.g., cancers and dementias, and also give birth to such diseases. For example, matrix metalloprotease (MMP) was recognized as a factor which degrades the extracellular matrix in a cell and in a human body. However, many researches have revealed that such MMP is involved in the cell movement in relation to the signal transfer of integrin and degradation of pericellular matrix. In addition, it has also been found out that the MMP plays an important role in the invasion and metastasis of cancer cells. As a result, various attempts for the new drug development are in progress around huge pharmaceutical companies in the developed countries.

Hence, as such new matrix proteins are found out, a variety of physiological functions of the protease group would be in the spotlight in future, whereby it is expected that new target proteins for new drugs can be found out.

However, no technique has not yet given to analyze the amount of specific protease activated and expressed in a quantitative imaging manner or to non-invasively image the degree of protease expressed in vivo, so associated technique development is in urgent need.

Representative methods of measuring protease being currently used may include a 2-D gel and multilevel liquid chromatography method, enzyme-linked immunosorbent assay (ELISA) method, or the like. Such methods, however, require multi-leveled measurement protocols such that it cannot be efficient to be used in screening many kinds of drugs, like developing new drugs. Moreover, such methods are not possible to be used in the early diagnosis of diseases because they detect the expression of unique protease in humans or quantitatively analyze the amount of expression thereof.

Accordingly, the present inventors have invented such a novel metal nanoparticle by which the expression of a unique protease can be detected in a human body or the amount of expression thereof can be quantitatively analyzed.

DISCLOSURE OF THE INVENTION

Technical Problem

Therefore, it is an object of the present invention to provide a metal nanoparticle having a peptide substrate specifically degraded by protease and fluorophore both bonded thereto, so as to selectively image protease expressed in cells and in tissues of humans, and the use thereof.

Also, it is another object of the present invention to provide a quantitative analysis method of protease using such metal nanoparticle, a cell imaging method, and a drug screening method for inhibiting protease overexpression.

Technical Solution

To achieve these objects, there is provided a metal nanoparticle to which peptide and fluorophore are coupled (bonded), in order to image protease expressed in cells and in tissues. The metal may be selected from gold, platinum, silver, tungsten or their derivatives, by which a quenching effect is generated with the fluorophore on the surface thereof.

The protease may include: MMP (matrix metalloproteinase) selected from the group consisting of MMP-1, MMP-2, MMP-3, MMP-7, MMP-8, MMP-9, MMP-10, MMP-11, MMP-12, MMP-13, MMP-14, MMP-15, MMP-16, MMP-17, MMP-18, MMP-19, MMP-20, MMP-21, MMP-22, MMP-23, MMP-24, MMP-25, MMP-26, MMP-27 and MMP-28; proteasome selected from the group consisting of 26S proteasome, 20S proteasome and S100 proteasome; lysomal protease selected from the group consisting of cathepsin-B, cathepsin-C, cathepsin-D, cathepsin-E, cathepsin-G, cathepsin-H and cathepsin-L; caspase involved in apoptosis, selected from the group consisting of caspase-1, caspase-2, caspase-3, caspase-4, caspase-5, caspase-6, caspase-7, caspase-8, caspase-9 and caspase-10; thrombin; and the like.

The peptide includes every already known peptide which is specifically degraded by the proteases. Such peptide includes the peptide existing in a matrix portion of an enzyme shown in a webpage (http://www.sigmaaldrich.com/Area_of_Interest/Biochemicals/Peptide_Explorer/Product_Lines/Other Enzyme Inhibitors.html#Other%20Enzyme%20 Substrates).

Also, the fluorophore, which is bonded to the metal nanoparticle to exhibit the quenching effect, may preferably be cyanine, fluorescein, tetramethylrhodamine, BODYPY or their derivatives.

In addition, the present invention provides an imaging method of protease in cells and in biologic tissues using the metal nanoparticle, a quantitative analysis method of protease, and a drug screening method of inhibiting protease overexpression.

Effect of the Invention

As described above, the present invention relates to a metal nanoparticle onto which peptide and fluorophore are chemically modified, in order to image the protease expressed in a cell and in a tissue. The metal nanoparticle has excellent bio-compatibility. The peptide is degraded by a specific protease, whereby the fluorophore exhibits fluorescence when the peptide is degraded. Hence, it is allowed for the metal nanoparticle of the present invention to rapidly screen activation and inhibition of the protease by imaging the protease. Also, the metal nanoparticle can selectively be absorbed in a cell and in a tissue, so as to be effectively used in the real-time cell images, the early diagnosis of non-invasive diseases and screening of drugs which inhibit the overexpression of the protease.

MODES FOR CARRYING OUT THE PREFERRED EMBODIMENTS

Hereinafter, description of the present invention is given in detail.

A gold nanoparticle according to the present invention has an excellent biocompatibility. To such a gold nanoparticle are bonded both a peptide substrate which uniquely reacts with various types of proteolytic enzymes and fluorophore. Accordingly, when the peptide substrate is degraded by a specific protease, fluorescence is emitted. Hence, the use of such gold nanoparticle can allow the imaging of activation and inhibition of the proteases for fast screening. Also, the metal nanoparticle can selectively be absorbed within a cell and within a tissue so as to be used in real-time cell imaging and non-invasive tissue imaging.

Fluorophore chemically coupled to the peptide substrate implements a quenching effect on the surfaces of the metal nanoparticle. Accordingly, if the peptide substrate is not degraded by a specific protease, the fluorophore does not become fluorescent. However, if the peptide substrate is degraded by reacting with the specific protease, then the fluorophore is separated from the surface of the metal nanoparticle, resulting in a disappearance of the quenching effect. Consequently, the fluorophore emits its own fluorescence, which allows the quantitative analysis of the protease. Preferably, the fluorophore being used herein emits red or near-infrared fluorescence and has a high quantum yield.

When such peptide-fluorophore derivatives are chemically coupled to the metal nanoparticle, preferably, they are coupled to each other so as to minimize a fluorescence intensity of the fluorophore due to a quenching effect which occurs by maintaining the distance between the fluorophore and the surface of the metal within several tens of nm on the surface of the metal nanoparticle. The fluorophore used in the present invention can be, for example, cyanine, fluorescein, tetramethylrhodamine, BODYPY or the like. Particularly, the cyanine group can be used the most preferably because they can emit and absorb near-infrared rays so as to minimize interruption or absorption with cells, blood, biologic tissues and the like.

The metal nanoparticle, which implements the quenching effect with the fluorophore on its surface, can thusly be selected from gold, platinum, silver, tungsten or their derivatives, and most preferably, gold. Gold salt ($HAuCl_4$) is reduced to sodium citrate ($C_6H_5Na_3O_7$-$2H_2O$) or Sodium Borohydride ($NaBH_4$) under surfactant, thereby preparing a stable gold nanoparticle having a size of 5 to 100 nm.

In order to acquire molecular-level images within a cell or tissue, it is possible to chemically reform a specific functional group representing unique images for a specific cell signal delivery to the metal nanoparticle. Typically, peptide derivatives which are selectively degraded by proteases are chemically synthesized with fluorophore implementing the quenching effect with the surface of the metal, thereby being capable of obtaining a precursor (peptide-fluorophore) having a unique degradability with respect to a specific protease. The precursor (i.e., peptide-fluorophore) is ultimately chemically modified onto the surface of the metal nanoparticle, thereby enabling the acquisition of a metal nanoparticle-peptide-fluorophore.

Here, the adjustment of the distance between the peptide-fluorophore and the surface of the metal nanoparticle can maximize the quenching effect which occurs on the metal nanoparticle, thereby preparing the metal nanoparticle-peptide-fluorophore so as to minimize the fluorescence of the fluorophore.

The metal nanoparticle-peptide-fluorophore has the peptide portion which is selectively degraded by a protease, and the thusly separated fluorophore functions on the principle which the fluorophore emits their own fluorescence when the distance with the metal nanoparticle is in the range of generating the quenching effect (e.g., more than 10 nm).

Such novel molecular imaging sensor may be applied to a variety of proteases within cells and tissues. As one example, the synthesis of fluorophore with the peptide, which is selectively degraded by matrix metalloproteinase (MMP) degrading an extracellular matrix around cancerous tissues, thrombin or proteasome generally existing in arteriosclerotic tissues or caspase activated upon a cell eradication, can induce the synthesis of various fluorescent functional groups. Upon modifying such various fluorescent functional groups onto the metal nanoparticles, new types of molecular imaging sensors implementing the fluorescence specifically for cancerous tissues, arteriosclerosis, cell eradication and the like can be developed.

In a detailed example of the present invention, peptide derivatives, which are specifically degraded by a MMP-2 among various MMPs overexpressed in a cancer cell so as to play a centric role for the proliferation or eradication of the cancer cell, were coupled to Cy5.5 as cyanine fluorophore emitting near-infrared fluorescence, thereby synthesizing the peptide-fluorophore. Such peptide-fluorophore was then ultimately chemically coupled to a gold nanoparticle. Accordingly, a molecular imaging sensor which emits near-infrared fluorescence by reacting with the MMP-2 was invented.

In order to prepare the gold nanoparticle-peptide-fluorophore derivatives, first, a preferable example of the peptide-fluorophore preparation may be indicated by Chemical Formula 1 as below:

A-B  [Chemical Formula 1]

where A denotes the fluorophore which may include fluorescein, BODYPY, alexa, cyanine and the like which can implement the quenching effect with the surface of the gold nanoparticle, and B denotes a peptide derivative which is specifically degraded by a specific protease. Such peptide-fluorophore can chemically be modified onto the gold nanoparticle by using SH group which exists in cyctein (Cys) endmost of the peptide. The preferable example thereof may be indicated by Chemical Formula 2 as follows:

-[A-B]$a$-C where A-B denotes the peptide-fluorophore derivative prepared in Chemical Formula 1, and C denotes a gold nanoparticle having a size of 5 to 100 nm. Here, the A-B derivative chemically modified onto the surface of the gold nanoparticle has a thickness of less than approximately a few tens of nm. a is in the range of 10 to 1000, wherein the number of a increases depending on the size of the gold nanoparticle.

The gold nanoparticle-peptide-fluorophore derivatives may create very stable nanoparticle in an aqueous solution. The fluorophore on the surface of gold is prepared with its fluorescence minimized due to the quenching effect. Such prepared gold nanoparticle has an excellent biocompatibility, can be controlled to be efficiently absorbed within a cell, and can passively be accumulated in a specific tissue or cell in vivo, so as to be used for different purposes, such as cell imaging, specific tissue imaging, drug delivery system and the like. Such composition can be applied both in vivo and in vitro. Also, it can be used for various purposes, such as a high-throughput screening required for a new drug development, early disease diagnosis and the like.

Hereinafter, the present invention will be described in detailed with reference to the below examples and experiments. The below examples and experiments are only exemplary, and are not limitative of the claims of the present application.

Example 1

Preparation of Gold Nanoparticle Exhibiting Specific Fluorescence with Respect to Protease A gold nanoparticle was prepared in a manner of reducing gold salt ($HAuCl_4$) to sodium borohydride ($NaBH_4$) in an aqueous solution. Peptide-fluorophore derivatives Cy5.5-Gly-Pro-Leu-Gly-Leu-Phe-Ala-Arg-Cys which are specifically degraded by MMP-2 were chemically bonded to the surface of gold, so as to prepare a nanoparticle exhibiting specifically near-infrared fluorescence onto MMP-2.

1-1. Preparation of Gold Nanoparticle 0.01 g of gold salt ($HAuCl_4$, $3H_2O$) was slowly mixed into 100 mL of boiling distilled water, and 2 mL of sodium citrate ($C_6H_5Na_3O_7$-$2H_2O$, 1 wt %) was added into the gold salt solution, to prepared gold nanoparticle. The shape and size of the gold nanoparticle were controlled by adjusting the concentration of the gold salt solution and the amount of the sodium citrate. The gold nanoparticle was prepared to have a diameter of 20 μm in the present invention.

1-2. Preparation of Fluorophore-Peptide Derivatives

The reaction of coupling the near-infrared fluorophore to the peptide may be indicated by Reaction Equation 1. The peptide was prepared by a Fmoc strategy in the order of Gly-Pro-Leu-Gly-Leu-Phe-Ala-Arg-Cys according to a solid phase synthesis. 20 mg of such prepared peptide was completely dissolved in 10 mL of dimethylsulfoxide (DMSO). Such was mixed with 20 mg of Cy5.5-NHS ester as near-infrared cyanine fluorophore, to which nitrogen was then charged to be reacted in a room temperature for a day. After the reaction, the Cy5.5-peptide was separated using HPLC. The separated Cy5.5-peptide was freeze-dried to be then coldly stored. Such prepared Cy5.5-peptide was measured through the HPLC and a mass spectrometry, and the fluorophore-coupled peptide was named Cy5.5-GPLGLFARC.

[Reaction Equation 1]

1-3. Preparation of Gold Nanoparticle-Peptide-Fluorophore

In order for such Cy5.5-GPLGLFARC synthesized in Example 1-2 to be chemically coupled to the surface of the gold nanoparticle, 0.1 mg of Cy5.5-GPLGLFARC was added into 10 mL of gold nanoparticle solution to react with each other at a room temperature for 16 hours, thereafter reacting in a solution containing 0.03 M of sodium chloride (NaCl), 0.1% of SDS (sodium dodecyl sulfate) and 0.01 M of phosphate for 24 hours. After the completion of the reaction, the thusly prepared gold nanoparticle-peptide-fluorophore was precipitated at 13000 rpm for 20 minutes by using a centrifugal separator, to be then washed up with distilled water for 5 times. The gold nanoparticle prepared was redistributed into a PBS solution to be then coldly stored. Such prepared gold nanoparticle (Cy5.5-GPLGLFARC-Gold) was named 'MMP selective gold nanosensor.'

Experiment 1. Particle Analysis of MMP Selective Gold Nanosensor

For the gold nanoparticle derivatives prepared in Example 1-3, the size of nanoparticle was measured using transmission electron microcopy (TEM) and light scattering (Brookhaven Instrument).

Figure 1:
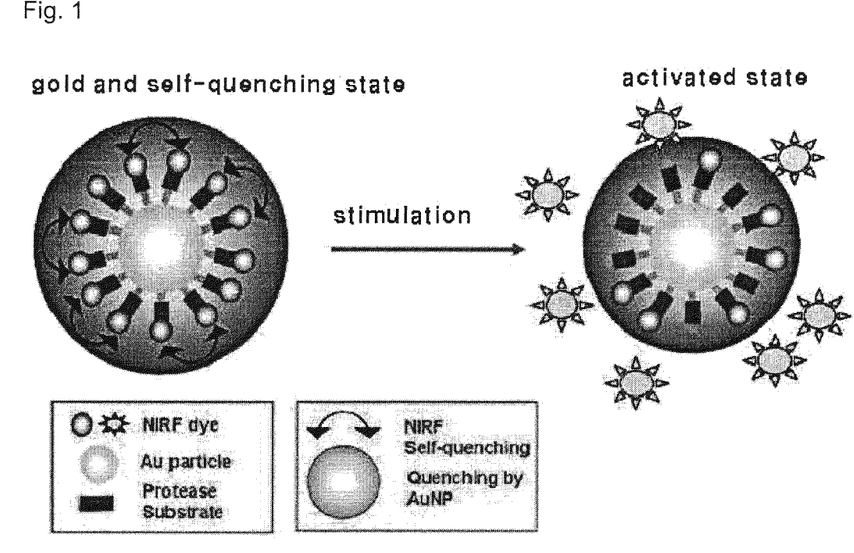
FIG. 1 illustrates a method of preparing a gold nanoparticle having peptides and near-infrared fluorophore (NIRF) which are specifically degraded by a protease prepared in the present invention.
Figure 2:
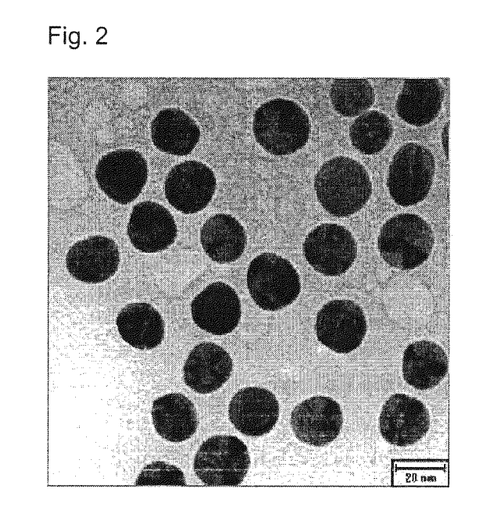
FIGS. 2 and 3 illustrate TEM images (transmission electron microscope) of a gold nanoparticle-peptide-fluorophore prepared in an Example 1-3 (see FIG. 2) and micelles thereof (see FIG. 3), wherein the micelle has a size of about 20 nm.
Figure 3:
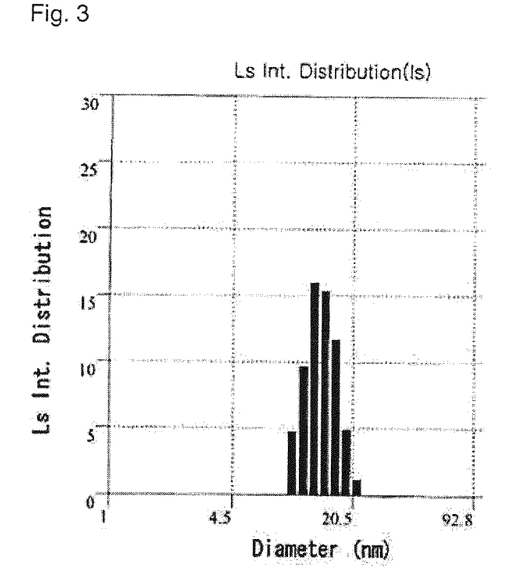

According to the experimental results, as shown in FIG. 2 and FIG. 3, the particle of the MMP selective gold nanosensor was shown to have the size of approximately 20 nm on the average.

Experiment 2. Optical Properties of MMP Selective Gold Nanosensor

The optical properties of the gold nanosensor prepared in Example 1-3, namely, a fluorescence quenching effect due to the gold nanoparticle and a selective fluorescence quenching effect with respect to a specific protease were observed.

2-1. Fluorescence Quenching Effect of Gold Nanosensor

In order to observe the optical fluorescence quenching effect of the gold nanosensor, the spectra of a gold nanosensor solution were observed using a spectrofluorometer (Shimadzu FL-600). An excitation spectrum was fixed to 675 nm, and then an emission spectrum was measured in the range from 680 nm to 780 nm. First of all, the gold nanosensor was dispersed in a PBS solution and thereafter the spectra thereof in the solution were observed. Also, a dithiothreitol (DTT) treatment was performed for such gold nanosensor dispersed solution and then the change in the spectra was observed. The DTT serves to separate the Cy5.5-peptide molecules from the surface of the gold nanoparticle, the Cy5.5-peptide molecules having been chemically coupled to the surface of the gold nanoparticle. Accordingly, if the changes in the two spectra are observed, the degree of the fluorescence quenching effect due to the gold nanoparticle can be yielded.

Figure 4:
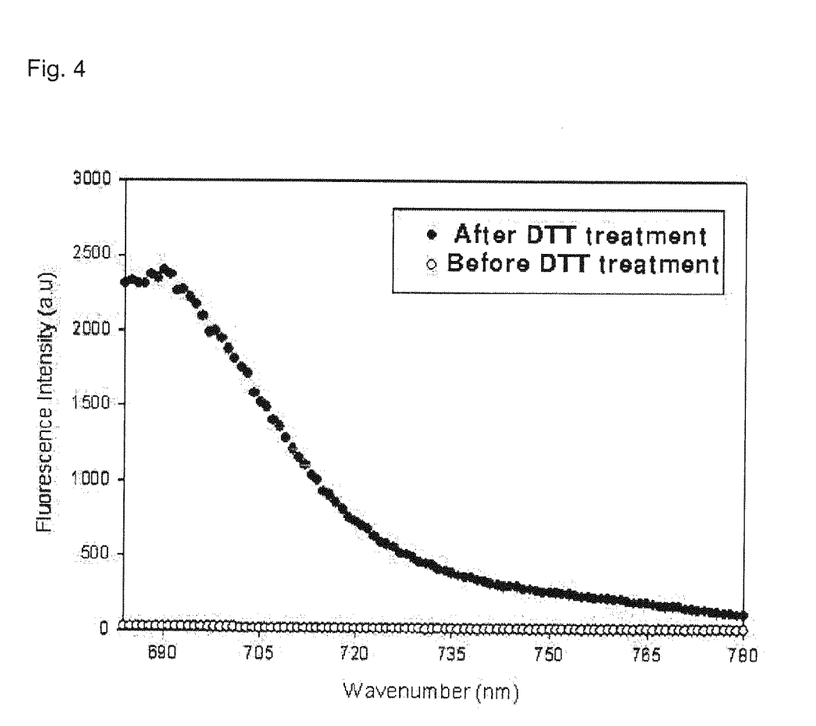
FIG. 4 illustrates spectroscopic properties of the gold nanoparticle-peptide-fluorophore prepared in the Example 1-3.

According to the results of the experiment, as shown in FIG. 4, it can be observed that approximately 100 times of the fluorescence quenching effect was yielded based on an emission spectrum measurement at 690 inn.

2-2. Change in Optical Property Due to Degradation of Gold Nanosensor Specific to MMP-2 Enzyme Selection specificity with respect to MMP-2 enzyme of MMP-2 selective gold nanosensor prepared in Example 1-3 was observed.

A gold nanosensor was reacted respectively with MMP-2 and MMP-13 each activated in the 96-well, a scramble peptide (i.e., a peptide having the same amino acid contained structure but having different sequence so as not to act as a substrate with respect to a specific enzyme) and MMP-2/ MMP-2 inhibitor at temperature of 37° C. for 2 hours, and thereafter a fluorescence exhibition due to the enzyme degradation was observed.

First, in order to activate the MMP-2 and MMP-13, the MMPs were added into a TCNB mixture (containing 0.1M of tris, 5 mM of calcium chloride, 200 mM of NaCl and 0.1% of Brij) having 2.5 mmol/L of p-aminophenyl mercuric acid added thereto, so as to be reacted at temperature of 37° C. for 1 hour. The activated MMP-2 and MMP-13 were reacted with the gold nanosensor in 200 μL of mixture in each well at temperature of 37° C. for 2 hours, and thereafter the degree of the fluorescence was observed using Kodak Image Station 4000MM Digital Imaging System built in a CD (Charge Coupled Device) camera.

Figure 5:
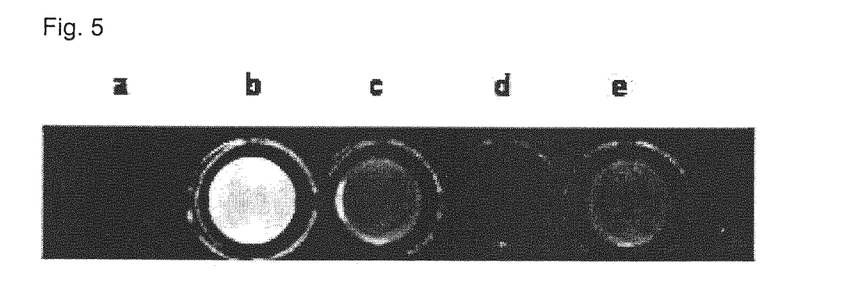
FIG. 5 illustrates fluorescent uniqueness of the gold nanoparticle that the gold nanoparticle of the present invention is specifically degraded by MMP-2 as a protease to thusly exhibit fluorescence.

According to the experimental results, it was observed as shown in FIG. 5 that fluorescence quenched in the state (a) that MMP-2 was not added but such bright fluorescence was exhibited as the peptide coupled to the gold nanosensor was selectively degraded in the state (b) that the MMP-2 was added. Under the same conditions, such the MMP-2 selective gold nanosensor rarely exhibits fluorescence with respect to MMP-13(c), but the gold nanosensor (d) containing the scramble peptide substrate used as a control group was not degraded in the MMP-2 added state, thereby exhibiting no fluorescence. It was also observed that no fluorescence is emitted in the reaction with MMP-2 inhibitor (e) which selectively prevents the MMP-2 activation. Hence, it could be confirmed that the MMP-2 selective gold nanoparticle prepared in Example 1-3 exhibited high fluorescence by selectively reacting with the MMP-2 enzyme.

2-3. Analysis of Protease Using Gold Nanosensor with Concentrations

The MMP gold nanosensor was used to quantitatively analyze the concentration of MMP-2 protease. In more detail, according to the same experimental way to that in Example 2-2, each of activated MMP-2s having concentrations of 0, 1.4, 3.5, 7 and 14 nmol/L, respectively, was added to the MMP-2 gold nanosensor to be reacted at temperature of 37° C. for 2 hours, and then the degree of the fluorescence was observed using the Kodak Image Station 4000MM Digital Imaging System.

Figure 6:
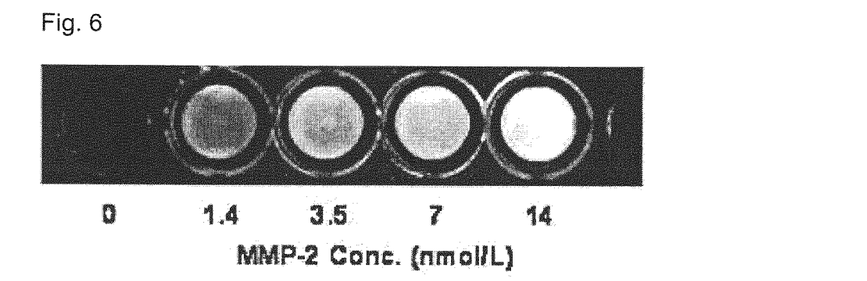
FIG. 6 illustrates that a protease can quantitatively be analyzed because of the unique increase in the degree of fluorescence in proportion to a concentration of a protease MMP-2.

According to the results of the experiment, as shown in FIG. 6, it was proved the fluorescence of the gold nanosensor increased in proportion to the concentration of the added MMP-2 enzyme, such that the concentration of a specific enzyme within a sample was expediently detected by measuring the fluorescence of the test group.

Experiment 3. Cancerous Tissue Imaging in Cancer Animal Models Using MMP Gold Nanosensor 3-1. Real-Time Imaging of Cancerous Tissue in Cancer Animal Models Invasive squamous cell carcinoma (SCC7) was injected into C3H/HeN mouse to create a cancer animal model. For the cancerous tissue with a size of more than 5 mm, the MMP-2 gold nanosensor was injected into the cancerous tissue, to thereafter estimate the possibility of imaging the cancer cell.

The invasive squamous cell carcinoma (SCC7) is known as a cancer cell expressing a great amount of MMP-2. The experiment was performed with respect to three animal test groups including a normal mouse having MMP-2 gold nanosensor (100 ul, 10 nM/mL) injected thereinto and a cancer mouse also having MMP-2 gold nanosensor (100 ul, 10 nM/mL) injected thereinto, and a cancer mouse having both MMP-2 gold sensor and MMP-2 inhibitor injected thereinto.

Figure 7:
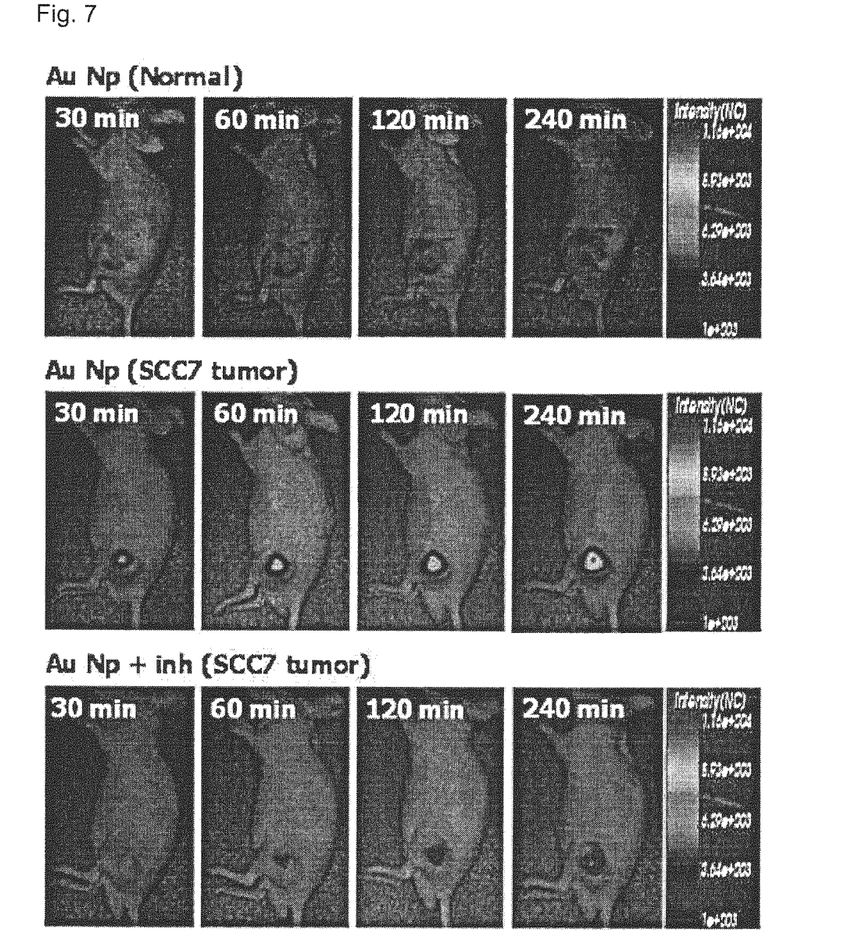
FIG. 7 illustrates that a gold nanoparticle of the present invention emits fluorescence in a mouse having a MMP-2-overexpressed cancer cell transplanted therein and the fluorescence becomes extinct upon the treatment with MMP-2 inhibitor which inhibits the MMP-2 activity, to thereby allow the imaging of the cancer diagnosis by an in vivo diagnosis of a specific protease.

According to the results of the experiment, as shown in FIG. 7, it was observed that the MMP-2 gold nanosensor injected into the normal mouse without the cancer cell did not exhibit fluorescence but the mouse with the cancer cell (Au NP(SCC7 tumor)) emitted high fluorescence as time elapses. Also, such high fluorescence exhibited in the MMP-2 expressed cancer cell was not emitted upon injecting the MMP-2 inhibitor inhibiting the MMP-2 activation (Au NP+inh (SCC7 tumor)). Consequently, it was proved that the MMP-2 gold nanosensor implemented high fluorescence by specifically reacting with the MMP-2 overexpressed cancer cell in vivo, and accordingly the cancer cell was able to be specifically imaged.

3-2. Fluorescence of Gold Nanosensor Specific for Cancerous Tissue

Depending on whether the MMP-2 inhibitor was injected into the cancerous tissue overexpressing MMP-2, the fluorescence of the MMP-2 gold nanosensor was observed.

The experiment for the mouse with the cancer cell was performed according to the same way to that in Example 3-1, and thereafter the cancerous tissue was removed both from the mouse having the MMP-2 inhibitor injected thereinto and from the mouse not having the MMP-2 injected thereinto, to thusly observe the specifically exhibited fluorescence in the cancer cell.

Figure 8:
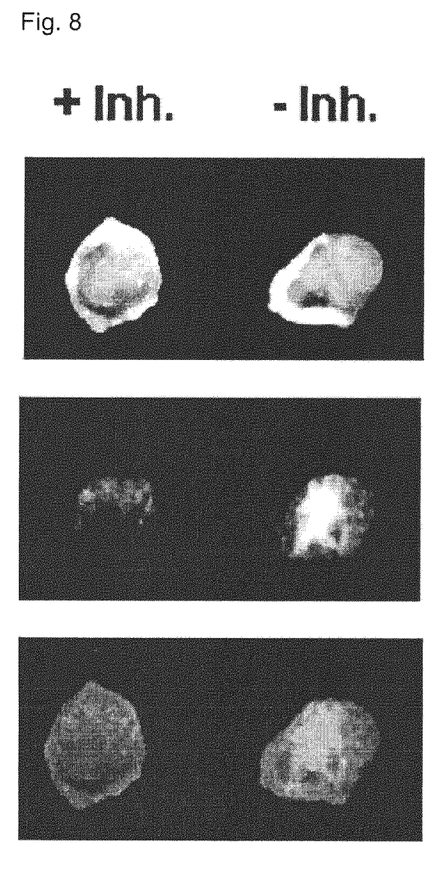
FIG. 8 illustrates that a MMP-2 gold nanosensor exhibits no fluorescence in a cancerous tissue having MMP-2 overexpressed, treated with MMP-2 inhibitor, but exhibits fluorescence in a cancerous tissue which is not treated with the MMP-2 inhibitor, to thereby allow a specific cancer diagnosis.

According to the results of the experiment, it was observed as shown in FIG. 8 that remarkably low fluorescence was exhibited in the cancerous tissue (+inh) treated with the MMP-2 inhibitor, while remarkably high fluorescence was exhibited in the cancerous tissue (−inh) not treated with the MMP-2 inhibitor. Hence, it was proved that the MMP-2 nanosensor exhibited the high fluorescence by specifically reacting with the MMP-2 overexpressed cancer cell so as to enable the unique imaging of such cancer cell.

The invention claimed is:

1. A metal nanoparticle having peptide and fluorophore for imaging protease expressed in a cell or a tissue, represented by the following formula:

[A-B]$_a$-C wherein A is a fluorophore,

B is a peptide substrate specifically degraded by the protease to be imaged, C is a metal nanoparticle, which is a quencher against the fluorophore, and a is an integer from 10 to 1000.

2. The metal nanoparticle of claim 1, wherein the metal is selected from gold, platinum, silver, tungsten or their derivatives, by which a quenching effect is generated with the fluorophore on the surface thereof.

3. The metal nanoparticle of claim 2, wherein the metal is gold.

4. The metal nanoparticle of claim 2, wherein the protease is MMP (matrix metalloproteinase), thrombin, proteasome, lysomal protease or caspase.

5. The metal nanoparticle of claim 4, wherein the MMP is MMP-1, MMP-2, MMP-3, MMP-7, MMP-8, MMP-9, MMP-10, MMP-11, MMP-12, MMP-13, MMP-14, MMP-15, MMP-16, MMP-17, MMP-18, MMP-19, MMP-20, MMP-21, MMP-22, MMP-23, MMP-24, MMP-25, MMP-26, MMP-27 or MMP-28;

the proteasome is 26S proteasome, 20S proteasome or S100 proteasome;

the lysomal protease is cathepsin-B, cathepsin-C, cathepsin-D, cathepsin-E, cathepsin-G, cathepsin-H or cathepsin-L; and the caspase is caspase-1, caspase-2, caspase-3, caspase-4, caspase-5, caspase-6, caspase-7, caspase-8, caspase-9 or caspase-10.

6. The metal nanoparticle of claim 1, wherein the protease is
MMP (matrix metalloproteinase), thrombin, proteasome, lysomal protease or caspase.

7. The metal nanoparticle of claim 6, wherein the MMP is MMP-1, MMP-2, MMP-3, MMP-7, MMP-8, MMP-9, MMP-10, MMP-11, MMP-12, MMP-13, MMP-14, MMP-15, MMP-16, MMP-17, MMP-18, MMP-19, MMP-20, MMP-21, MMP-22, MMP-23, MMP-24, MMP-25, MMP-26, MMP-27 or MMP-28;

the proteasome is 26S proteasome, 20S proteasome or S100 proteasome;

the lysomal protease is cathepsin-B, cathepsin-C, cathepsin-D, cathepsin-E, cathepsin-G, cathepsin-H or cathepsin-L; and the caspase is caspase-1, caspase-2, caspase-3, caspase-4, caspase-5, caspase-6, caspase-7, caspase-8, caspase-9 or caspase-10.

8. The metal nanoparticle of claim 1, wherein the fluorophore exhibits a
quenching effect by being coupled to the metal nanoparticle.

9. The metal nanoparticle of claim 8, wherein the fluorophore is cyanine, fluorescein, tetramethylrhodamine, BODYPY or their derivatives.

* * * * *